(12) United States Patent
Kaimal et al.

(10) Patent No.: US 6,342,626 B1
(45) Date of Patent: Jan. 29, 2002

(54) PROCESS FOR THE PREPARATION OF ALKYL ESTERS FROM COMMERCIAL LACTIC ACID

(75) Inventors: Thengumpillil Narayana Balagopala Kaimal; Penumarthy Vijayalakshmi; Bandi Ramalinga; Ayyagari Ananta Laxmi, all of Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/774,761

(22) Filed: Jan. 31, 2001

(51) Int. Cl.$^7$ ............................................. C07C 69/66
(52) U.S. Cl. ....................................... 560/179; 560/189
(58) Field of Search .................................. 560/178, 189

(56) References Cited

U.S. PATENT DOCUMENTS

| | | | |
|---|---|---|---|
| 5,210,296 A | * | 5/1993 | Cockrem |
| 5,247,059 A | * | 9/1993 | Gruber et al. |
| 5,274,073 A | * | 12/1993 | Gruber et al. |

* cited by examiner

*Primary Examiner*—Paul J. Killos
(74) *Attorney, Agent, or Firm*—Baker Botts L.L.P.

(57) ABSTRACT

The present invention relates to a catalyst-free process for the conversion of commercial lactic acid to alkyl ester of carbon $C_1$ to $C_8$ which comprises simultaneous hydrolysis of dimers or highpolymers of lactic acid present in commercial lactic acid to free lactic acid and esterification of free lactic acid with an alcohol in the presence of water at a temperature in the range of 130–250° C. for 4–11 hrs at a pressure of 5–25 kg/cm$^2$, to obtain desired esters.

18 Claims, No Drawings

PROCESS FOR THE PREPARATION OF ALKYL ESTERS FROM COMMERCIAL LACTIC ACID

FIELD OF THE INVENTION

The present invention relates to a process for the preparation of alkyl ester from commercial lactic acid. The present invention particularly relates to a catalyst-free improved process for the conversion of aqueous commercial lactic acid containing free acid, dimer or highpolymers of lactic acids to alkyl ester by reaction with alcohol.

BACKGROUND AND PRIOR ART REFERENCES

Esters of lactic acid are high boiling liquids with properties of interest as solvents and as plasticizers for cellulose plastics and vinyl resins. Butyl lactate is used as a high boiling solvent in lacquer formulations. The advantages of lactic acid and its esters in cosmetics and toiletries formulations have been reported (Manufac. Chem., 1999, May, 18–19). Lactate esters can be regarded as a new generation of skin whitening agents that have been shown to produce a synergistic effect when combined with other skin whitening agents (Purac Products—Brochures, www.purac.com.). Lactate esters are used to meet the high quality demands of semiconductor industry as a safe solvent in photoresist and in edgebead removal formulations (Purac Products—Brochures, www.purac.com.). A valuable way of producing butyl acrylate is by dehydration of butyl lactate (Manufacturing Chemist, 1999, May, 18–19; J. Chem. Tech. Biotech., 1994, 59, 149–156). Butyl lactate is used as a co-surfactant in preparation of microemulsions with anionic surfactants (J. Disp. Sci. Tech., 1997, 18, 161–175). Detergent compositions containing carbonate and/or lactate esters are useful for removal of pitch, wax polishing materials and protective films from the optical parts (CA, 1997, 126, 159058s). Lactate esters are used as non-inflammable and mild odor solvent cleaners (U.S. Pat. No. 5,604,196). Lactate esters especially calcium stearyl lactate enhances the shelf life and organoleptic characteristics of starchy food [JP 07,203,834]. Alkyl lactates are used for degreasing surfaces and defluxing of circuit boards contaminated by soldering fluxes (CA, 1990, 112, 58912c). Lactic acid esters are useful in the preparation of herbicidal formulations (CA, 1991, 115 29370z; WO, 91,00,278). Dopamine derivative formulated with lactic acid esters, fatty acid monoglycerides and/or higher alcohols showed high permeability through the rat skin in vitro (CA, 1991, 115, 239731u; EP-431942; JP-317, 343). An invention related to butyrate prodrugs prepared from methyl lactate and butyrylchloride is described (CA, 1997, 126, 321080s, WO 97 12,855). Ethyl lactate can be used in the treatment of acne and against seborrhoea [Acta Dermat. (Stockholm), 1972, 52, 406). Esterification of crude lactic acid and subsequent hydrolysis to produce lactic acid is reported as a procedure for purification of lactic acid.

Many methods are described in prior art for conversion of lactic acid to alkyl esters. Reaction between lactic acid and alcohols or carboxylic acids catalyzed by lipase from *Candida antarctica* with hexane as solvent was reported (Biotechnol. Lett. 1997, 19, 315–317). The authors found lactic acid to be a good acyl donor and esters of both primary and secondary alcohols were synthesized. Dimer formation due to lactic acid acting as both nucleophile and acyl donor was not observed. Butyl lactate was synthesized using heterogeneous supported hetero polyacid catalyst, $PW_{12}/SiO_2$ (Huaxue Yu Nianhe, 1996, 3, 128–130). Japanese patents (JP-05, 155,816; JP-05, 140,039) describe preparation of ethyl lactate from lactonitrile with water and sulfuric or phosphoric acid followed by esterification with ethanol. U.S. Pat. No. 5,264,617 report synthesis of butyl lactate by depolymerization of polylactide by heating with butanol in the presence of p-toluene sulfonic acid. European Patent [EP 517,571] describes esterification of ammonium lactate with methanol at reduced pressure. Japanese Patent (JP 07,258, 154) describes that autoclaving a mixture of lactamide, Zr oxide and methanol at 200° C. and 34 atm for 2 hr give methyl lactate in 97.8% selectivity at 94.3% conversion. A process for manufacture of ethyl lactate for use in food industry is described in a patent [CN 1,102,180] with a catalyst comprising of H-type acidic resin complex of glycerin or ethylene glycol and boric acid, sodium dihydrogen phosphate in weight ratio of 1:(0.5–1.0):(0.1–0.2). The process comprises reacting 80% lactic acid and ethanol (92–93%) in the presence of the catalyst. A research paper describes the kinetics of liquid phase synthesis and hydrolysis of butyl lactate catalyzed by cation exchange resin [J. Chem. Technol. Biotechnol, (1994) 59, 149–50]. Japanese Patent (JP 07,10,805) describes preparation of hydroxy carboxylic acid ester in a two phase system of aqueous lactic acid and alcohol like butanol in the presence of inorganic salt like sodium chloride and sulfuric acid catalyst at room temperature with vigorous stirring for 2 h to give yield of 70% butyl lactate and the yield was 37% without sodium chloride. n-Butyl lactate was synthesized with solid super strong acid catalyst derived from sulfuric acid and $TiO_2$ (CA, 1995, 122, 190924n). Method of producing lactic acid and lactic acid esters is described in European Patent (EP 614,983). The process involves fermentation of a culture medium with ammonia and adjusting pH of the culture medium with ammonia and to the resulting ammonium lactate solution is added butanol or pentanol and heating the resultant mixture thereby inducing esterification of lactic acid with alcohol and at the same time effecting liberation and recovery of ammonia and adding a mineral acid to promote complete esterification.

Synthesis of butyl lactate was studied by Chinese researchers [Synthetic Commu., 1994, 24, 3269–75] with super acid resin catalyst $D001-AlCl_3$ (sulfonated cross linked polystyrene macroporous strong acid cation exchange resin). German Patent [Ger Off DG 4,341,770] describes a process for preparation of high purity lactate esters via the lactic acid or its salts followed by esterification, wherein the fermented product is neutralized with alkaline earth carbonates or bicarbonates and byproducts removed by treatment with ammonia and $CO_2$ and the purified ammonium lactate solution is esterified. Catalytic synthesis of n-butyl lactate with rare earth sulfate was studied [Huaxue Shijie, 1998, 39, 199–201]. The esterification of n-butanol with lactic acid yielded >85% butyl lactate.

Japanese Patent [JP, 08 40,983] claims synthesis of lactic acid ester by reaction of lactide with alcohol in the presence of strong acidic ion exchange resin. Yet another patent [WO, 91-11527, CA, 1992, 116, 5328m] describes production of lactic acid esters which comprises (a) formation of ammonium lactates with lactic acid forming organisms in the presence of ammonia, (b) reacting ammonium lactate with alcohol and gaseous $CO_2$ to esterify ammonium lactate and (c) recovering pure lactic acid ester. Synthesis of lactates by using modified HZSM-5, as catalyst is reported (CA, 1995, 123,116189f). A new technique of preparation of ethyl lactate by rectification method was reported to increase the yield to over 95% (CA, 1996, 124, 235465y).

According to a Japanese Patent (JP 08,208,565) a mixture of aqueous lactic acid, ethanol and p-toluene sulphonic acid was heated at 160° C. and ethanol and water were removed by distillation to give a solution having acid value of 1.9 mg KOH/g which was mixed with NaOH/EtOH and distilled to give product having acid value 0.1 mg KOH/g with 85% yield. Lactic acid esters are prepared by hydrogenation of glycidic acid ester with Pd/C in EtOH at r.t. in 66% yield [JP-08,73,407]. Ethyl and butyl lactates were prepared in yield of >90% using strongly acidic cation exchanger 732 and D72 as catalyst by reacting the acid and alcohol in a molar ratio of 1:3.5 and the catalyst concentration was 60% that of lactic acid [Talyuan Gongye Faxue Xuebao, 1990, 21, 43–6].

Alpha-acetoxypropionic acid and methanol are fed to a reaction medium that contains an acid catalyst kept at specific temperature and the reaction is conducted as the product, methyl lactate, is distilled off (JP 571,40,745; U.S. 45,00,727). Esterification of lactic acid with methanol in the presence of acidic catalyst at 30–300° C. and 0.01 to 30 bar is patented [DE 3,222,837].

US Patent reports the preparation of desired lactate from lactamide and formate [U.S. Pat. No. 5,824,818].

Thus, the earlier methods for preparation of alkyl esters from commercial lactic acid use either homogeneous or heterogeneous catalysts. Raw materials like lactonitrile, polylactide, ammonium lactate, lactamide etc. are also used.

The earlier processes involve either the use of acid catalyst which needs additional neutralization step in case of homogenous catalyst or filtration step in case of heterogeneous catalyst.

Some of the processes involve the use of cation exchange resin, which also requires pretreatment.

Some processes require stringent conditions such as adjustment of pH or an addition of inorganic salt like sodium chloride to increase the yield.

Some processes require two-step reaction of the starting material like hydrolysis of lactonitrile with acid followed by esterification with alcohol or formation of ammonium lactate from lactic acid and ammonia followed by its esterification in the presence of carbon dioxide.

Development of a catalyst free process would be economically advantageous and Eco-friendly.

OBJECTS OF THE INVENTION

The main object of the present invention is to provide a process for the preparation of alkyl ester from aqueous solution of commercial lactic acid.

Another object of the present invention is to use the ester thus obtained after distillation as a solvent, as a plasticizer for cellulose plastics and vinyl resins, and for pharmaceutical and cosmetic applications.

Still another object of the present invention is that the process has particular application to the simultaneous esterification of free lactic acid in admixture with dimer and high polymers of lactic acid even in the presence of water.

DETAILED DESCRIPTION

Accordingly, the present invention provides a process for the conversion of commercial lactic acid to alkyl ester which comprises simultaneous hydrolysis of dimer and highpolymers of lactic acid to free lactic acid and esterification of free lactic acid, by reaction with alcohol at a temperature in the range of 130–250° C. for 2 to 8 hrs at a pressure of 20–25 kg/cm$^2$ such as herein described.

In an embodiment, the esterification process comprising the following steps a) charging the commercial lactic acid containing free lactic acid, dimer and highpolymers and water with an alcohol in to an autoclave, b) heating the reaction mixture to about temperature ranging from 130 to 250° C. for 2 to 8 hours at a pressure ranging between 15–25 kg/cm$^2$, c) monitoring the reaction using GC analysis by determining the acid number, d) cooling the contents, removing the excess alcohol by distillation and repeating the steps a) to c) with fresh alcohol, and e) distilling the final contents to obtain the desired ester.

The term commercial lactic acid used, in the specification means the lactic acid commercially available in the market and this generally includes free lactic acid (65–80% by wt), dimers or highpolymers (10–25% by wt) of lactic acid and water (5 to 20% by wt).

In an embodiment of the present invention, the commercial lactic acid used, is a mixture of free lactic acid (65–80% by wt), dimers or highpolymers (10–25% by wt) of lactic acid and water (5 to 20% by wt).

In an embodiment of the present invention, the commercial lactic acid used is preferably a mixture of free lactic acid 73% by wt, dimers or highpolymers of lactic acid 15% by wt and water 12% by wt.

In an embodiment of the present invention, a one-stage catalyst-free process is carried out involving both the steps of hydrolysis and esterification simultaneously.

In another embodiment of the present invention, the process is economically advantageous and eco-friendly.

In yet another embodiment of the present invention, the process involves the simultaneous esterification of free lactic acid in admixture with dimer and highpolymers of lactic acid in a single step.

In yet another embodiment of the present invention, the process involves the conversion of the free, dimer, and highpolymers of lactic acid even in the presence of substantial amount of water to alkyl esters.

In yet another embodiment of the invention, the process involves reacting aqueous solution of free acid and dimer and highpolymers of lactic acid with various alcohols to get different esters.

In yet another embodiment, the esterification of the acid is carried out with $C_1$ to $C_8$ alcohols.

In yet another embodiment there is employed an excess of 1.5 to 10 moles of alcohol based on lactic acid, more preferably an excess of 2.2 moles of alcohol.

In yet another embodiment, the reaction is carried out in an autoclave and there is employed an autogenous pressure.

In yet another embodiment, the temperature employed ranges between 130–250° C., more preferably 180–210° C.

In yet another embodiment, the reaction is carried out for a period ranging from 4–11 hrs, more preferably 2–8 hrs.

The following examples are given by way of illustration and therefore should not be construed to limit the scope of the present invention.

EXAMPLE 1

Commercial lactic acid (405 g) of acid value, 481 and 360 ml of methanol were charged to a 2 L stainless steel autoclave equipped with a stirrer, temperature control and sampling device. Commercial lactic acid contains free lactic acid 73% by wt, dimers or highpolymers of lactic acid 15% by wt and water 12% by wt. The contents were heated to 200° C. and the reaction was further continued at this temperature for 5 hrs at a pressure of 20 kg/cm$^2$. Progress of the reaction was monitored by GC analysis and by determining the acid number (mg KOH/g). After the reaction the contents were cooled and the product was analyzed for acid number. About 80% of the reaction were completed at this stage. To complete the reaction, excess of methanol was distilled out and the product subjected to a second treatment as described above after adding fresh methanol. When GC analysis did not show any peak corresponding to the starting material the reaction was assumed as completed. The product after completion of second stage was distilled and pure methyl lactate fraction was collected and analyzed by GC and $H^1$-NMR.

EXAMPLE 2

The reaction was conducted as in example 1 except that the ratio of lactic acid to methanol (wt/vol) was 1:1.5 and they were charged to a 2 L stainless steel autoclave equipped with a stirrer, temperature control and sampling device. The contents were heated to 200° C. and the reaction was further continued at this temperature for 5 hrs at a pressure of 18 kg/cm$^2$. Progress of the reaction was monitored by GC analysis and by determining the acid number (mg KOH/g). After the reaction the contents were cooled and the product was analyzed for acid number. About 80% of the reaction were completed at this stage. To complete the reaction, excess of methanol was distilled out and the product subjected to a second treatment as described above after adding fresh methanol. When GC analysis did not show any peak corresponding to the starting material the reaction was assumed as completed. The product after completion of second stage was distilled and pure methyl lactate fraction was collected and was analyzed by GC and $H^1$-NMR.

EXAMPLE 3

The reaction was carried out as in example 1 except that the ratio of lactic acid to methanol (wt/vol) was 1:3 and they were charged to a 2 L stainless steel autoclave equipped with a stirrer, temperature control and sampling device. The contents were heated to 200° C. and the reaction was further continued at this temperature for 5 hrs at a pressure of 25 kg/cm$^2$. Progress of the reaction was monitored by GC analysis and by determining the acid number (mg KOH/g). After the reaction the contents were cooled and the product was analyzed for acid number. About 80% of the reaction was completed at this stage. To complete the reaction, excess of methanol was distilled out and the product subjected to a second treatment as described above after adding fresh methanol. When GC analysis did not show any peak corresponding to the starting material the reaction was assumed as completed. The product after completion of second stage was distilled and pure methyl lactate fraction was collected and was analyzed by GC and $H^1$-NMR.

EXAMPLE 4

The reaction was carried out as in example 1 except that the alcohol used was butanol and they were charged to a 2-L stainless steel autoclave equipped with a stirrer, temperature control and sampling device. The contents were heated to 200° C. and the reaction was further continued at this temperature for 5 hrs at a pressure of 13 kg/cm$^2$. Progress of the reaction was monitored by GC analysis and by determining the acid number (mg KOH/g). After the reaction the contents were cooled and the product was analyzed for acid number. About 80% of the reaction was completed at this stage. To complete the reaction, excess of butanol was distilled out and the product subjected to a second treatment as described above after adding fresh butanol. When GC analysis did not show any peak corresponding to the starting material the reaction was assumed as completed. The product after completion of second stage was distilled and pure butyl lactate fraction was collected and was analyzed by GC and $H^1$-NMR.

EXAMPLE 5

The reaction was carried out as in example 1 except that the alcohol used was 2-ethyl hexanol and they were charged to a 2 L stainless steel autoclave equipped with a stirrer, temperature control and sampling device. The contents were heated to 200° C. and the reaction was further continued at this temperature for 5 hrs at a pressure of 10 kg/cm$^2$. Progress of the reaction was monitored by GC analysis and by determining the acid number (mg KOH/g). After the reaction the contents were cooled and the product was analyzed for acid number. About 80% of the reaction were completed at this stage. To complete the reaction, excess of 2-ethyl hexanol was distilled out and the product subjected to a second treatment as described above after adding fresh 2-ethyl hexanol. When GC analysis did not show any peak corresponding to the starting material the reaction was assumed as completed. The product after completion of second stage was distilled and pure 2-ethyl hexyl lactate fraction was collected and was analyzed by GC and $H^1$-NMR.

THE MAIN ADVANTAGES OF THE PRESENT INVENTION ARE

1. The present invention is a catalyst free one step process for the simultaneous conversion of dimer and highpolymers of lactic acid to free lactic acid by hydrolysis and esterification of free lactic acid to alkyl lactate by reaction with alcohols.

2. The reaction is carried out with commercial lactic acid having a total acidity of 88% (free acid, 73%).

3. As no catalyst is used, there is no generation of aqueous effluents as in the case of homogeneous catalysts. Hence the process is more environmentally friendly.

What is claimed is:

1. A process for the conversion of commercial lactic acid to alkyl ester of carbon $C_1$ to $C_8$ which comprises simultaneous hydrolysis of dimers or highpolymers of lactic acid present in commercial lactic acid to free lactic acid and esterification of free lactic acid with an alcohol in the presence of water at a temperature in the range of 130–250° C. for 4–11 hrs at a pressure of 5–25 kg/cm$^2$, to obtain desired ester.

2. A process as claimed in claim 1 wherein the commercial lactic acid used is a mixture of free lactic acid (65–80% by wt), dimers or highpolymers (10–25% by wt) of lactic acid and water (5–20% by wt).

3. A process as claimed in claim 2 wherein the commercial lactic acid used is preferably a mixture of free lactic acid 73% by wt, dimers or highpolymers of lactic acid 15% by wt and water 12% by wt.

4. A process as claimed in claim 1 wherein, the alcohol used is selected from the group consisting of straight chain, branched-chain alcohol and polyols.

5. A process as claimed in claims 1 wherein, the alcohol used is selected from monohydric or polyhydric alcohol.

6. A process as claimed in claims 1 wherein, the free lactic acid is esterified with an alcohol selected from $C_1$–$C_8$ alcohol.

7. A process as claimed in claims 1 wherein, the ratio of acid to alcohol is ranging from 1:1 to 1:10.

8. A process as claimed in claim 1 wherein, the alcohol used is more than 1.5 to 10 moles based on lactic acid.

9. A process as claimed in claim 1 wherein, the alcohol used is more than 2.2 moles based on lactic acid.

10. A process as claimed in claim 1 wherein, the reaction is carried out in an autoclave under an autogenous pressure.

11. A process as claimed in claim 1 wherein, the reaction is carried out at a temperature range between 180–210° C.

12. A process as claimed in claim 1 wherein, the reaction is carried out for a period ranging from 4–11 hrs.

13. A process as claimed in claim 1 wherein, the reaction is carried out for a period ranging from 2–8 hrs.

14. A process as claimed in claims 1 wherein the esterification is carried out in the presence or absence of water.

15. A process as claimed in claims 1 wherein, the yield of esters ranges from 80–90%.

16. A process as claimed in claim 1 wherein, the esters are methyl lactate, ethyl lactate, butyl lactate, 2-ethyl hexyl lactate and other esters.

17. A process for the conversion of a commercial lactic acid to alkyl ester of carbon $C_1$ to $C_8$, comprising the following steps
  a) charging a commercial lactic acid containing free lactic acid, dimer and highpolymers of lactic acid and water with an alcohol in to an autoclave,
  b) heating the reaction mixture to about temperature ranging from 130 to 250° C. for 2 to 8 hours at a pressure of 15–25 kg/cm$^2$,
  c) monitoring the reaction using GC analysis by determining the acid number,
  d) cooling the contents, removing the excess alcohol by distillation and repeating the steps a) to c) with fresh alcohol, and
  e) distilling the final contents to obtain the desired ester.

18. A process as claimed in claim 17, the esters thus obtained after distillation is used as solvent, as a plasticizer for cellulose plastics and vinyl resins, and for pharmaceutical and cosmetic applications.

* * * * *